US008664270B2

(12) United States Patent
Long et al.

(10) Patent No.: US 8,664,270 B2

(45) Date of Patent: Mar. 4, 2014

(54) CLOG RESISTANT INSECT CONTROL FORMULATIONS HAVING TERMINAL DIYNE ACETYLENIC HYDROCARBON AND PYRETHRIN

(75) Inventors: Lina Long, Mount Prospect, IL (US); Brian W. Anderson, Racine, WI (US); Gerald W. Cummings, Pleasant Prairie, WI (US); Jamie T. Huynh, Franklin, WI (US)

(73) Assignee: S.C. Johnson & Son, Inc., Racine, WI (US)

(*) Notice: Subject to any disclaimer, the term of this patent is extended or adjusted under 35 U.S.C. 154(b) by 0 days.

(21) Appl. No.: 13/486,023

(22) Filed: Jun. 1, 2012

(65) Prior Publication Data

US 2013/0324604 A1 Dec. 5, 2013

(51) Int. Cl.

*A01N 53/02* (2006.01)

*A01P 7/04* (2006.01)

(52) U.S. Cl.

USPC .......... 514/531; 424/409

(58) Field of Classification Search

USPC .......... 424/409; 514/531

See application file for complete search history.

(56) References Cited

U.S. PATENT DOCUMENTS

| | | | | |
|---|---|---|---|---|
| 2,421,223 | A | 5/1947 | Smith et al. | |
| 2,841,625 | A | 7/1958 | Burch et al. | |
| 2,958,709 | A | 11/1960 | Wotiz | |
| 3,076,040 | A | 1/1963 | Skeeters | |
| 3,235,577 | A * | 2/1966 | Adams et al. | 554/35 |
| 3,839,561 | A | 10/1974 | Bordenca | |
| 3,943,239 | A | 3/1976 | Yamaguchi et al. | |
| 4,081,468 | A | 3/1978 | Baker et al. | |
| 4,125,400 | A | 11/1978 | Downer et al. | |
| 4,220,640 | A | 9/1980 | Zweig et al. | |
| 4,320,139 | A | 3/1982 | Takei et al. | |
| 4,515,768 | A | 5/1985 | Hennart et al. | |
| 4,798,825 | A | 1/1989 | Evans | |
| 4,874,787 | A | 10/1989 | Yamamoto et al. | |
| 5,647,053 | A | 7/1997 | Schroeder et al. | |
| 6,074,656 | A | 6/2000 | Katsuda et al. | |
| 6,391,329 | B1 * | 5/2002 | Ito et al. | 424/409 |
| 7,744,833 | B2 | 6/2010 | Varanasi et al. | |
| 8,137,715 | B2 | 3/2012 | Shah et al. | |
| 2009/0101730 | A1 * | 4/2009 | Davis et al. | 239/44 |

FOREIGN PATENT DOCUMENTS

| | | | |
|---|---|---|---|
| FR | 2738718 | | 3/1997 |
| FR | 2738718 | A1 * | 3/1997 |
| WO | WO2004/068945 | | 8/2004 |
| WO | WO2005/070203 | | 8/2005 |
| WO | WO 2008/035029 | | 3/2008 |

OTHER PUBLICATIONS

G. Pieper et al., Photostabilization of Bioethanomethrin, Resmethrin, and Natural Pyrethrins (Pyrethrum) by Mixed Diaryl-p-phenylenediamines, 30 J. Agric. Food Chem. 405-407 (1982).

K. Georgieff et al., The Relative Inhibitory Effect of Various Compounds on the Rate of Polymerization of Vinyl Acetate . . . , 8 Journal of Applied Polymer Science 889-896 (1964).

K. Georgieff, Polymerization Activity Test for Methyl Methacrylate, 8 Journal of Applied Polymer Science 503-509 (1964).

F. Ballistreri et al., Oxidation of Acetylene to Glyoxal by Dilute Hydrogen Peroxide, 48 Tetrahedron 9999-100002 (1992).

K. Mastovska et al., Evaluation of Common Organic Solvents for Gas Chromatographic Analysis and Stability of Multiclass Pesticide Residues, 1040 J. Chromatography 259-272 (2004).

J. Ryu et al., Alkyne Oxidation by Nonheme Iron Catalysts and Hydroperoxides, 7 Inorg. Chem. Com. 534-537 (2004).

K. Georgieff, The Relative Inhibitory Effect of Certain Acetylene Polymers on the Rate of Polymerization of Acrylonitrile and Vinyl Acetate, 78 J. Poly. Sci. 589-592 (1954).

PCT Search Report mailed Jul. 19, 2013 in the corresponding application PCT/US2013/041528, 16 pages.

7964 Pyrethrins in The Merck Index, 14th edition; Jan. 1, 2006pp. 1369-1370.

A. Glynne-Jones; Pyrethrum; 5 Pesticide Outlook, vol. 12 195-198 (2001).

John Wiley & Sons; 1147: Di-t-butyl-p-methylphenol in Gardner's Commercially Important Chemicals: Synonyms, Trade Names, and Properties pp. 192-193; Jan. 1, 2005.

John Wiley & Sons; 1337: Dilauryl 3,3'-thiodipropionate in Gardner's Commercially Important Chemicals: Synonyms, Trade Names, and Properties p. 222; Jan. 1, 2005.

John Wiley & Sons; 408: Bis(2-hydroxy-3-tert-butyl-5-methylphenyl) methane in Gardner's Commercially Important Chemicals: Synonyms, Trade Names, and Properties p. 72 (Jan. 1, 2005).

F.M. Hanna Ali et al., Evaluation of Antioxidant and Antimicrobial Activity of Aloysia Triphylla; Electronic Journal of Environmental, Agricultural and Food Chemistry pp. 2689-2699 (Aug. 1, 2011).

Sigma Aldrich web site excerpt entitled "1,8-Nonadiyne MSDS", pp. 1-7 dated Nov. 28, 2012.

Sigma Aldrich web site excerpt entitled "1,7-Octodiyne", pp. 1-7 dated Nov. 28, 2012.

Sigma Aldrich web site excerpt entitled "1,6-Heptadiyne MSDS", pp. 1-7 dated Dec. 18, 2012.

* cited by examiner

*Primary Examiner* — Janet Epps-Smith
*Assistant Examiner* — Courtney Brown

(57) ABSTRACT

Disclosed are pyrethrin-based insect control compositions which have been formulated to reduce wick clogging. An acetylenic hydrocarbon having at least two terminal alkyne groups, such as 1,8-nonadiyne, together with an antioxidant such as dilauryl thiodipropionate, are used to reduce clogging caused by components of pyrethrum extract.

10 Claims, 3 Drawing Sheets

| Components | Aged (Hours) | Time to Knockdown % of the Mosquitoes (Mean+/-SD) | |
|---|---|---|---|
| | | KT50 (min) | KT80 (min) |
| 4%Pyrethrin, 5%BHT | 8 | 8.00+/- 0.35 | 9.25+/- 0.71 |
| 4%Pyrethrin, 5%BHT | 389 | 6.00+/- 0.53 | 8.00+/- 0.35 |
| 4%Pyrethrin, 1%DLTP, 1%1,8-nonadiyne | 389 | 4.33+/- 0.18 | 5.25+/- 0.17 |

FIG. 3

CLOG RESISTANT INSECT CONTROL FORMULATIONS HAVING TERMINAL DIYNE ACETYLENIC HYDROCARBON AND PYRETHRIN

CROSS-REFERENCE TO RELATED APPLICATIONS

Not applicable

STATEMENT REGARDING FEDERALLY SPONSORED RESEARCH/DEVELOPMENT

Not applicable

BACKGROUND OF THE INVENTION

The present invention relates to devices that dispense a pyrethrin-based insect control formulation from a porous wick. More particularly, it relates to providing formulations (and formulation impregnated wicks) for use with such devices, where the formulations include a mix of pyrethrin and an acetylenic hydrocarbon, and as a result reduce the tendency of pyrethrin-based formulations to clog the wick.

Pyrethrum is an insecticide obtainable from a natural plant source. It is typically extracted from a chrysanthemum plant in a form that contains pyrethrin I (see FIG. 1), pyrethrin II, cinerin I, cinerin II, jasmolin I and jasmolin II, usually with some impurities. In some cases one or more of pyrethrin I or II is isolated from the extract, and used separately. More often, the overall pyrethrum extract is used.

Chrysanthemum plants can be grown and harvested in an environmentally friendly (e.g. sustainable) manner, and pyrethrum extract can be obtained from them at relatively low cost. Also, because it is obtained from an essentially natural source, pyrethrum extract has a somewhat wider regulatory and public perception acceptance than a number of more synthetic insect control ingredients do.

To dispense pyrethrum/pyrethrins one typically dissolves the extract in a solvent (e.g. an isoparaffinic hydrocarbon material such as an Isopar), places the resulting solution in a reservoir such as a bottle, extends a porous wick through a cap of the bottle into the liquid, slowly attracts the active/solvent mix out of the reservoir via the wick to an exposed end of the wick, and then drives an active/solvent mix off the exposed end of the wick into the environment (e.g. most typically using a heater system such as that of U.S. Pat. No. 5,647,053). The heater system could be supplemented with a blower if desired (e.g. compare the fan system of U.S. Pat. No. 7,444, 833).

Unfortunately, pyrethrum extract impurities tend to react (largely through oxidation and polymerization reactions) to form materials that can clog a dispensing wick. This is in part due to impurities typically found in the extract being oxidized and/or polymerized to clogging materials, and in part because some pyrethrum extract core active components are susceptible to unwanted oxidation/polymerization, again leading to formation and deposition of nonvolatile components in the evaporation zone of the wick that cause wick clogging.

Wick clogging reduces the effectiveness of this type of dispensing device over time, eventually reducing the air release rate of pyrethrin from device, and consequently reducing mosquito repellency. As a result, some consumers may not be satisfied with the performance of conventional pyrethrum-impregnated wicks absent further improvements.

In U.S. Pat. No. 4,798,825 it was disclosed that certain acetylenic substances accelerated pyrethrin decomposition, and thus it was important to remove or modify such materials when using pyrethrin to avoid premature decomposition of pyrethrin.

For example, selective hydrogenation could reduce undesired peroxy species in pyrethrum extract.

In any event, a need exists to address the pyrethrin-related wick clogging concern, without introducing other unacceptable disadvantages (while maintaining the advantages of using pyrethrum).

BRIEF SUMMARY OF THE INVENTION

In one aspect the invention provides an insect control formulation. It contains an insect control ingredient comprising pyrethrin (e.g. a pyrethrin extract containing one or more of pyrethrin I and II), a solvent that the ingredient is carried in (e.g. an isoparaffinic hydrocarbon such as Isopar), and an acetylenic hydrocarbon having a HC≡C moiety at two termini of the acetylenic hydrocarbon, such that the acetylenic hydrocarbon is a diyne.

The acetylenic hydrocarbon may be linear or branched, and may have more than two HC≡C moieties. In one preferred form it has the following formula: $H—C≡C—(CH_2)_x—C≡C—H$, where x is a number from 1 to 20. Most preferably the acetylenic hydrocarbon is 1,8 nonadiyne (where x is 5).

In other preferred forms there is also an antioxidant or radical chain stopper such as dilauryl thiodipropionate, butylated hydroxytoluene and 2,2'-methylenebis(6-tert-butyl-4-methylphenol). This enhances the effect of the acetylenic hydrocarbon.

It is preferred that the pyrethrin containing ingredient be about 2 to 10% by weight of the formulation (e.g. about 4%), the acetylenic hydrocarbon be about 0.1 to 4% by weight of the formulation, the solvent be about 80 to 95% by weight of the formulation, and other ingredients (e.g. an antioxidant or a fragrance such as myrcene) be the remainder.

In another form the invention provides a wick for dispensing such an insect control formulation. There is a porous wick body (e.g. a cylindrical rod), and the insect control formulation is positioned in pores of the wick body.

In other aspects the invention provides a wick for dispensing such an insect control formulation. There is a porous wick body and such an insect control formulation positioned in pores of the wick body. One can use a sintered glass material for the wick body (e.g. available from Porex). Alternatively, other inert porous wick substrates can be used for the body, such as nylons. While it is also possible to use wicks made from wood material, that is not preferred as wood wicks are exposed to conditions during manufacture that may produce oxygenated species that could accelerate the degradation of the pyrethrin.

In sum, it has been discovered that adding a hydrocarbon with two terminal alkyne groups to a pyrethrum based insect control formulation reduces certain undesired reactions (oxidation/polymerization), and thereby reduces wick clogging caused by the results of those undesired reactions. Without limiting the scope of the invention, it is believed that some of these reactions are inhibited by the scavenging of impurity metals and/or interference with a peroxide reaction.

The insect control formulations of the present invention can be initially positioned in pores of a porous wick by causing the wick to attract the formulation from a reservoir (by capillary attraction). The wick can project down into the insecticidal formulation in the reservoir, and also extend externally upward/outward. The external portion of the wick can then be positioned next to a means for driving the active off the wick (e.g. most preferably a heater).

The invention thereby renders the use of pyrethrin (especially natural extract pyrethrum containing pyrethrins) more practical as a substitute for synthetic pyrethroids when controlling various insects such as mosquitoes, and also thereby opens up the possibility of providing a more natural insect control formulation. It also extends the life of wicks used with such pyrethrin-based materials Moreover, the formulations of the present invention have an improved knockdown efficiency above and beyond what one might expect from just the capabilities of the acetylenic hydrocarbon per se, or effects related to minimizing the clogging problem. This is likely because the terminal diyne acetylenic hydrocarbon also protects the pyrethrin-based material from degradation (not just protects against the impurities forming clogging materials).

The foregoing and other advantages of the present invention will be apparent from the following description. As these embodiments are merely illustrative, they are not intended to represent the full scope of the invention. Thus, reference should therefore be made to the claims herein for interpreting the scope of the invention.

DRAWINGS

FIG. 3 is a chart summarizing knockdown experiments comparing results from prior art formulations and a formulation of the present invention.

DETAILED DESCRIPTION OF THE PREFERRED EMBODIMENTS

Figure 1:
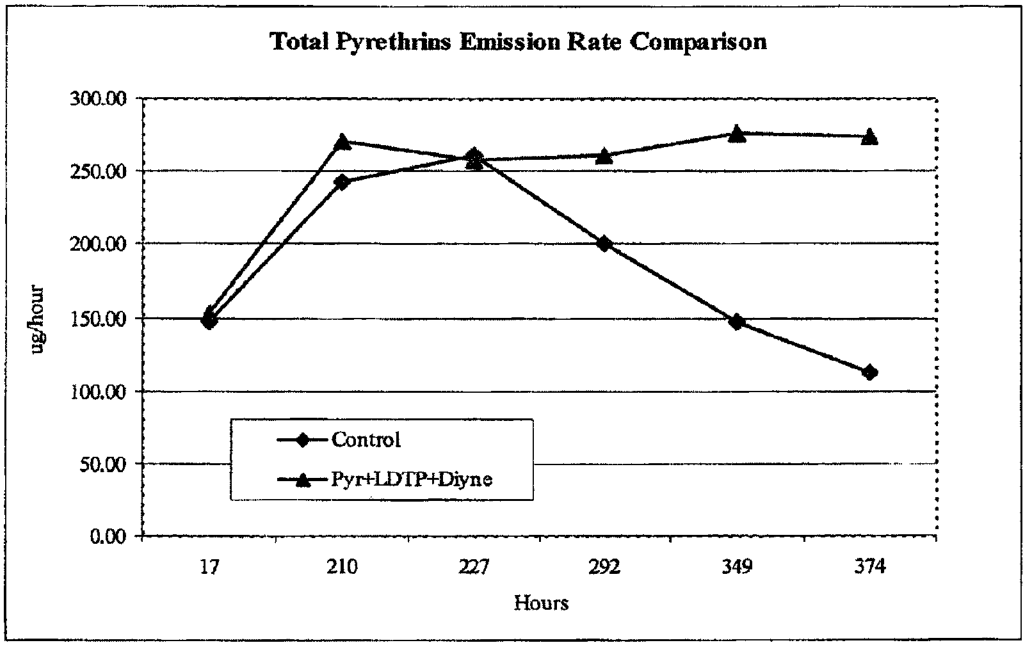
FIG. 1 is a graph comparing the emission rate over time of a wick having a prior art pyrethrin-based formulation with that of related formulations modified in accordance with the present invention.

A test formulation was prepared containing 8% of a 50% solution of pyrethrum extract (4% active), 1% 1,8-nonadiyne, 1% dilauryl thiodipropionate and 90% Isopar V isoparaffinic hydrocarbon. This was compared (as shown in FIG. 1) with another formulation, but with the LTDP and diyne replaced with about 5% BHT. A sintered glass wick was selected and the resulting test showed similar results for about 225 hours, followed by a drop off in effectiveness in the standard control system thereafter, indicating clogging.

Figure 2:
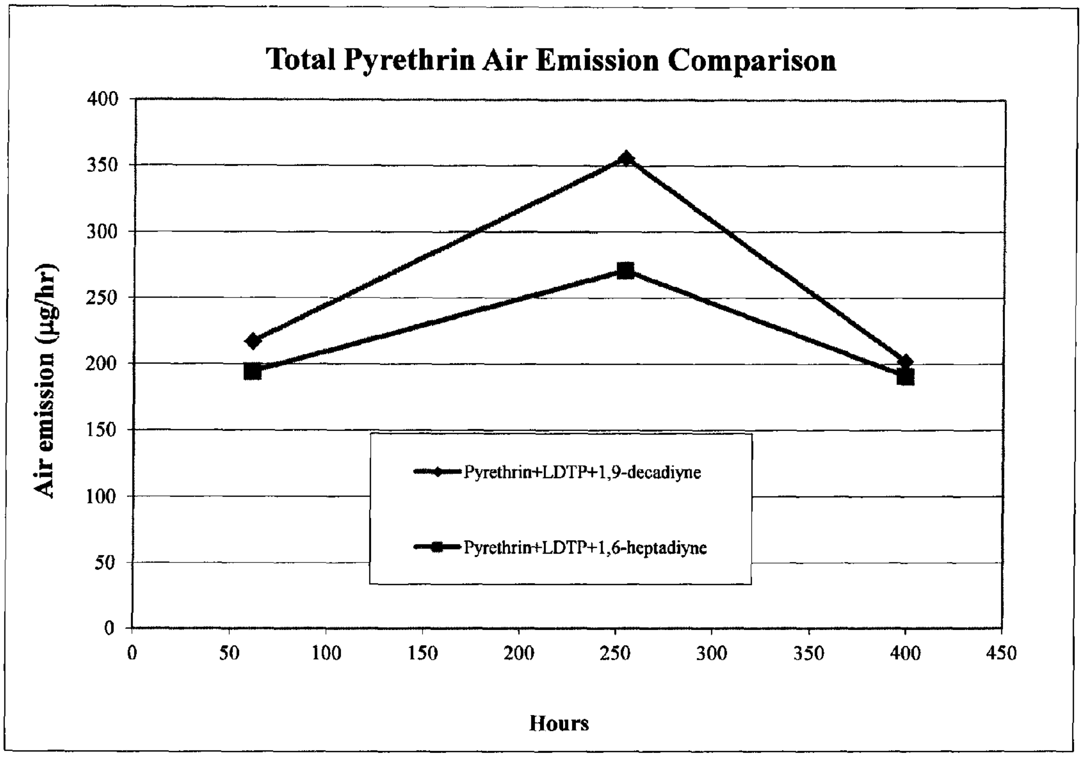
FIG. 2 is similar to FIG. 1, but showing efficacy of two other diynes.

Additional similar tests evaluated 1,6-heptadiyne and 1,9-decadiyne as noted on FIG. 2. Again, extended utility after 225 hours was noted.

"Knockdown" is a measure of how much time it takes a population of insects to experience a certain percentage of the insects being knocked down when exposed to the insect control ingredient. The lower the number, the quicker the control, and the more effective the formulation. The knockdown capability of formulations containing nonadiyne against mosquitoes was tested, and results are as summarized in FIG. 3. As can be seen, there was significantly faster knockdown versus controls.

It is believed that these results are due in part to inhibiting oxidation and/or polymerization impurities in pyrethrum. Further, portions of pyrethrin I and II have terminal conjugated double bonds which are believed to be particularly susceptible to radical attack (yielding materials more likely to cause clogging). The use of the terminal diyne acetylenic hydrocarbons appears to inhibit this, thereby further reducing clogging, and thus leaving more pyrethrin to control insects.

While the preferred embodiments of the present invention have been described above, it should be appreciated that there are other embodiments within the spirit and intended scope of this disclosure. For example, the acetylenic hydrocarbon can be used with or without additional antioxidants and/or radical chain stoppers.

Moreover, while specific tests have been run on a number of acetylenic hydrocarbons, it is believed that various other acetylenic hydrocarbons with multiple terminal alkyne group (s) will have similar benefits such as 1,5-hexadiyne, 1,6-septadiyne, and 1,7-octadiyne. Of course, still other acetylenic hydrocarbons may be suitable for particular applications (e.g. longer molecules, with or without additional triple bond moieties beyond terminal diyne features).

Regardless, the invention is not to be limited to just the specific embodiments shown or described.

INDUSTRIAL APPLICABILITY

Provided herein are improved pyrethrin-based insect control formulations that are stabilized to minimize clogging characteristics, and wicks for delivering them.

All documents cited in this document are, in relevant part, incorporated herein by reference. The citation of any document is not to be construed as an admission that it is prior art with respect to the present invention.

What is claimed is:

1. An insect control formulation comprising:
an insect control ingredient comprising pyrethrin;
a solvent that the ingredient is carried in; and
an acetylenic hydrocarbon having a HC≡C moiety at two termini of the acetylenic hydrocarbon.

2. The insect control formulation of claim 1, wherein the insect control ingredient is pyrethrum extract.

3. The insect control formulation of claim 1, wherein the acetylenic hydrocarbon is a diyne.

4. The insect control formulation of claim 1, wherein the acetylenic hydrocarbon has the following formula:

$$H—C≡C—(CH_2)_x—C≡C—H,$$

where x is a number from 1 to 20.

5. The insect control formulation of claim 4, wherein the acetylenic hydrocarbon is a nonadiyne.

6. The insect control formulation of claim 1, wherein the solvent is an isoparaffinic hydrocarbon solvent.

7. The insect control formulation of claim 1, further comprising a material selected from the group consisting of dilauryl thiodipropionate and 2,2'-methylenebis(6-tert-butyl-4-methylphenol).

8. A wick for dispensing an insect control formulation, comprising:
a porous wick body;
an insect control formulation positioned in pores of the wick body, the formulation comprising:
an insect control ingredient comprising pyrethrin;
a solvent that the ingredient is carried in; and
an acetylenic hydrocarbon having a H≡C moiety at two termini of the acetylenic hydrocarbon.

9. The wick of claim 8, wherein the acetylenic hydrocarbon has the following formula:

$$H—C≡C—(CH_2)_x—C≡C—H,$$

where x is a number from 1 to 20.

10. The wick of claim 8, wherein the porous wick body comprises a material selected from the group consisting of sintered glass and nylon.

* * * * *